(12) United States Patent
Brown

(10) Patent No.: US 8,706,220 B2
(45) Date of Patent: Apr. 22, 2014

(54) METHOD AND APPARATUS FOR DETECTING AND TREATING TACHYARRHYTHMIAS INCORPORATING DIAGNOSTIC/THERAPEUTIC PACING TECHNIQUES

(75) Inventor: Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 959 days.

(21) Appl. No.: 12/100,157

(22) Filed: Apr. 9, 2008

(65) Prior Publication Data
US 2009/0259269 A1  Oct. 15, 2009

(51) Int. Cl.
*A61N 1/362* (2006.01)

(52) U.S. Cl.
USPC .............................. 607/14; 607/9

(58) Field of Classification Search
USPC ...................................... 607/14, 9
See application file for complete search history.

(56) References Cited

U.S. PATENT DOCUMENTS

| | | | |
|---|---|---|---|
| 4,272,877 A | 6/1981 | Takeuchi et al. | |
| 4,316,472 A | 2/1982 | Mirowski et al. | |
| 4,375,817 A | 3/1983 | Engle et al. | |
| 4,384,585 A | 5/1983 | Zipes | |
| 4,577,633 A | 3/1986 | Berkovits et al. | |
| 4,587,970 A | 5/1986 | Holley et al. | |
| 4,726,380 A | 2/1988 | Vollmann et al. | |
| 4,800,883 A | 1/1989 | Winstrom | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |
| 5,117,824 A | 6/1992 | Keimel et al. | |
| 5,148,812 A | 9/1992 | Verrier et al. | |
| 5,163,427 A | 11/1992 | Keimel | |
| 5,243,980 A | 9/1993 | Mehra | |
| 5,411,530 A | 5/1995 | Akhtar | |
| 5,462,060 A | 10/1995 | Jacobson et al. | |
| 5,545,186 A | 8/1996 | Olson et al. | |
| 5,713,932 A | 2/1998 | Gillberg et al. | |
| 5,755,736 A | 5/1998 | Gillberg et al. | |
| 5,846,263 A * | 12/1998 | Peterson et al. | 607/14 |
| 5,855,593 A | 1/1999 | Olson et al. | |
| 5,991,656 A | 11/1999 | Olson et al. | |
| 6,052,620 A | 4/2000 | Gillberg et al. | |
| 6,141,581 A | 10/2000 | Olson et al. | |
| 6,178,350 B1 | 1/2001 | Olson et al. | |
| 6,259,947 B1 | 7/2001 | Olson et al. | |
| 6,272,377 B1 | 8/2001 | Sweeney et al. | |

(Continued)

FOREIGN PATENT DOCUMENTS

WO  92/18198  10/1992

*Primary Examiner* — Joseph Stoklosa
(74) *Attorney, Agent, or Firm* — Michael C. Soldner

(57) ABSTRACT

An implantable medical device (IMD) and methods of operating the same to treat a tachyarrhythmia are disclosed herein. In accordance with this method, an arrhythmia of the heart is classified based on one or more supraventricular tachycardia (SVT) rejection rules, which differentiate between a first group of heart rhythms that do not require treatment and a second group of heart rhythms that possibly require treatment. Diagnostic/therapeutic pacing can then be performed to further discriminate the second group of heart rhythms as being within a first sub-group of heart rhythms and a second sub-group of heart rhythms which are to be treated by applying a ventricular tachycardia (VT)/ventricular fibrillation (VF) therapy sequence. In another implementation, the order in which the IMD performs diagnostic/therapeutic pacing and analyzes passive detection and classification criteria can be reversed.

14 Claims, 8 Drawing Sheets

(56) References Cited

U.S. PATENT DOCUMENTS

| | | |
|---|---|---|
| 6,487,443 B2 | 11/2002 | Olson et al. |
| 6,490,478 B1 | 12/2002 | Zhang et al. |
| 6,567,691 B1 | 5/2003 | Stadler |
| 6,731,978 B2 | 5/2004 | Olson et al. |
| 6,876,880 B2 | 4/2005 | Hess et al. |
| 6,879,856 B2 | 4/2005 | Stadler et al. |
| 6,892,094 B2 | 5/2005 | Ousdigian et al. |
| 6,922,584 B2 | 7/2005 | Wang et al. |
| 6,980,860 B2 | 12/2005 | Stadler et al. |
| 7,031,771 B2 * | 4/2006 | Brown et al. ............... 607/14 |
| 7,039,463 B2 | 5/2006 | Marcovecchio |
| 7,076,289 B2 | 7/2006 | Sarkar et al. |
| 7,083,588 B1 | 8/2006 | Shmulewitz et al. |
| 7,103,405 B2 | 9/2006 | Sarkar et al. |
| 7,130,677 B2 | 10/2006 | Brown et al. |
| 2001/0034538 A1 | 10/2001 | Olson et al. |
| 2002/0065473 A1 | 5/2002 | Wang et al. |
| 2003/0125772 A1 | 7/2003 | Olson et al. |
| 2003/0191404 A1 * | 10/2003 | Klein ............... 600/518 |
| 2004/0172067 A1 | 9/2004 | Saba |
| 2004/0220624 A1 | 11/2004 | Ritscher et al. |
| 2004/0249420 A1 | 12/2004 | Olson et al. |
| 2007/0260283 A1 | 11/2007 | Li |
| 2007/0293894 A1 | 12/2007 | Zhang et al. |
| 2008/0051843 A1 | 2/2008 | Li et al. |

* cited by examiner

METHOD AND APPARATUS FOR DETECTING AND TREATING TACHYARRHYTHMIAS INCORPORATING DIAGNOSTIC/THERAPEUTIC PACING TECHNIQUES

TECHNICAL FIELD

Embodiments of the subject matter described herein relate generally to implantable medical devices (IMDs). More particularly, embodiments of the subject matter relate to IMDs which detect, classify and/or treat various types of tachyarrhythmia.

BACKGROUND

A tachyarrhythmia generally refers to a heart rate that is faster than 100 beats per minute. Tachyarrhythmias can be either physiologic such as sinus tachycardia occurring during exercise or pathologic as during atrial or ventricular tachycardia which can occur when irritable cells in the heart muscle or heart's electrical conduction system start to fire faster than the heart's normal rhythm. Tachyarrhythmias can start in either the upper heart chambers (atria) or lower heart chambers (ventricles). An atrial tachyarrhythmia starts in the atria and is generally classified as being atrial tachycardia (AT), atrial flutter, or atrial fibrillation (AF). A ventricular tachyarrhythmia starts in the ventricles and is generally classified as being either a ventricular tachycardia (VT) or ventricular fibrillation (VF). VT and VF can diminish the ability of the ventricles to pump blood to the body, which can lead to a quick depletion of oxygen to the body, a potentially life-threatening condition.

Implantable medical devices (IMDs) are well known in the medical device field. The prior art is replete with IMDs that are designed to monitor heart activity, detect tachyarrhythmia, provide pacing therapy, and/or provide defibrillation therapy. One type of IMD is known as an implantable cardioverter-defibrillator (ICD). An ICD is a device that is implanted in patients who are at high-risk of sudden cardiac death to provide prompt defibrillation to patients who experience VT/VF episodes. The ICD monitors the rate and rhythm of the heart and can deliver therapies, including defibrillation, when the rhythm is determined to be VT or VF.

Early ICDs were single chamber, and discriminated heart rhythms on the basis of heart rate alone. Slower tachycardias (e.g., <150 beats per minute) were considered to be supraventricular tachycardia (SVT) and received no therapy. Tachycardias between 150 and 190 beats per minute, in a typical usage, were classified as ventricular tachycardias and received rate-appropriate therapy. Tachycardias faster than 190 beats per minute were classified as VF and received defibrillation therapy. Heart rates of SVTs and VTs overlap as do heart rates of VT and VF. Therefore, it was common for therapy to be delivered when none was needed when using rate-only detection schemes. More recently, new criteria have been developed to improve discrimination between SVTs and VTs/VFs to help reduce the frequency of inappropriate therapy. These criteria included, for example, rate of onset (e.g., how quickly the heart increases), rate stability (e.g., how consistent the ventricular intervals are) and electrogram morphology (e.g., how similar the QRS complex is to SVT or VT).

Dual chamber ICDs were introduced that monitor the rate and pattern of both atrial and ventricular activity. These ICDs use sophisticated algorithms to determine whether the rhythm is SVT, requiring no therapy, or VT/VF, requiring therapy. One example of a dual chamber ICD is described in U.S. Pat. No. 7,031,771, issued to Brown et al. on Apr. 18, 2006, and is incorporated herein by reference in its entirety.

In addition, numerous detection and classification systems have been proposed. Many ICDs implement detection and classification strategies that identify heart events, event intervals or event rates as they occur as being indicative of the likelihood of the occurrence of specific types of arrhythmias, with each type of arrhythmia having a preset group of criteria which must be met precedent to detection or classification. As events progress, the criteria for identifying the various arrhythmias are all monitored simultaneously, with the first set of criteria to be met resulting in detection and diagnosis of the arrhythmia.

It is desirable to provide methodologies for identifying and distinguishing various types tachyarrhythmia from one another and for providing appropriate therapies to treat the identified tachyarrhythmia.

BRIEF SUMMARY

In one embodiment, an implantable medical device (IMD) is configured for implanted operation in the body of a patient and related operating methods are provided.

According to one embodiment, a method is provided for operating an implantable medical device (IMD) to treat a tachyarrhythmia. In accordance with this method, an arrhythmia of the heart is classified based on one or more supraventricular tachycardia (SVT) rejection rules, which differentiate between a first group of heart rhythms that do not require treatment and a second group of heart rhythms that possibly require treatment. Diagnostic/therapeutic pacing can then be performed to further discriminate the second group of heart rhythms as being within a first sub-group of heart rhythms and a second sub-group of heart rhythms which are to be treated by applying a ventricular tachycardia (VT)/ventricular fibrillation (VF) therapy sequence.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
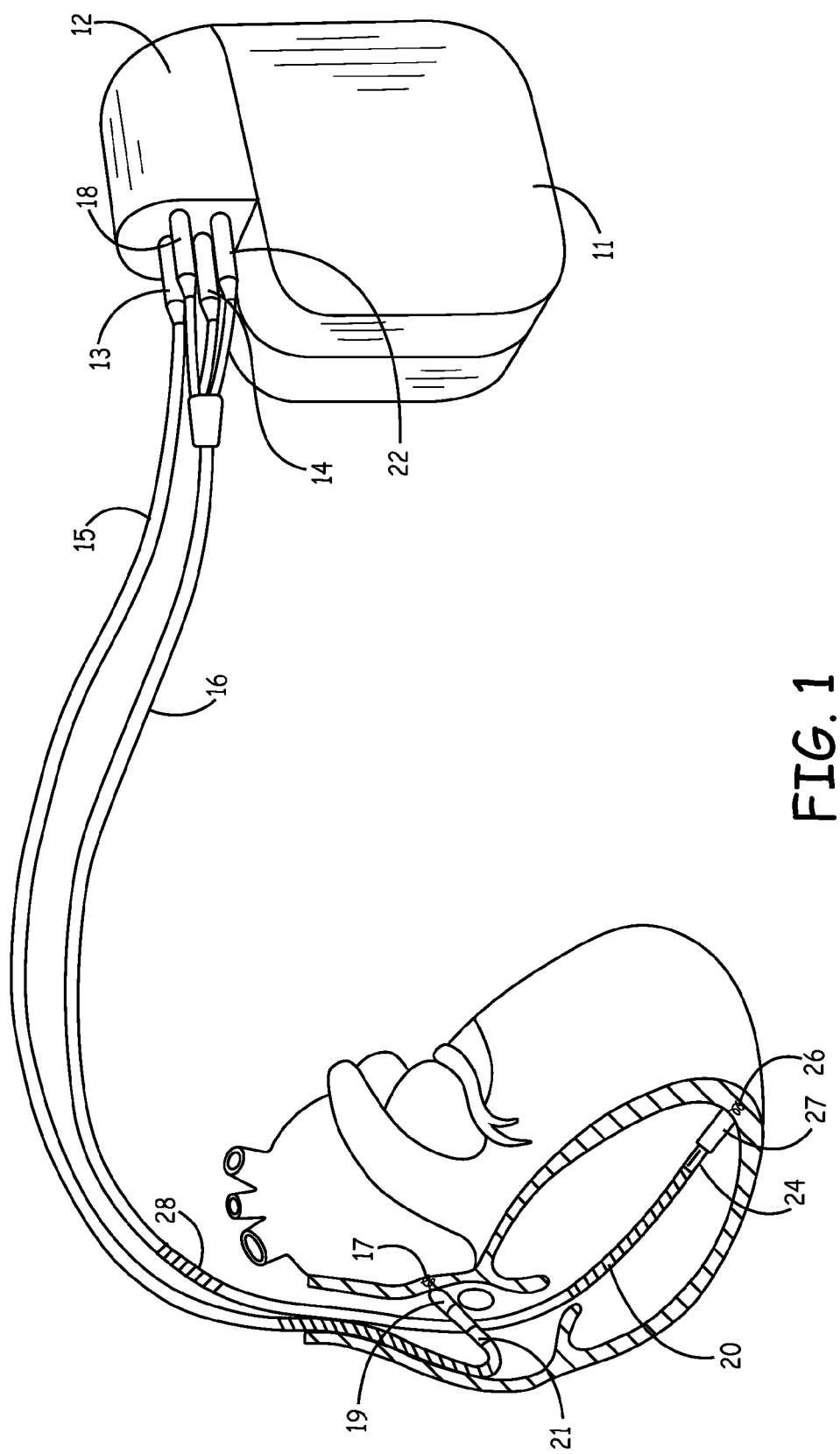
FIG. 1 illustrates an implantable medical device (IMD)

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

Techniques and technologies may be described herein in terms of functional and/or logical block components and various processing steps. It should be appreciated that such block components may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments may be practiced in conjunction with any number of IMD configurations, medical device therapies, and monitoring/diagnostic equipment, and that the system described herein is merely one suitable example.

For the sake of brevity, conventional techniques related to signal sensing and signal processing, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the subject matter. The following description refers to elements or nodes or features being "connected" or "coupled" together. As used herein, unless expressly stated otherwise, "connected" means that one element, node, feature is directly joined to (or directly communicates with) another element, node, feature, and not necessarily mechanically. Likewise, unless expressly stated otherwise, "coupled" means that one element, node, feature is directly or indirectly joined to (or directly or indirectly communicates with) another element, node, feature, and not necessarily mechanically. Thus, although the schematics depict exemplary arrangements of elements, additional intervening elements, devices, features, or components may be present in an embodiment of the depicted subject matter.

The system embodiments may be described herein with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the systems described herein (which may reside at an IMD, an external monitor device, or elsewhere in the system environment) are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links.

FIG. 1 illustrates an implantable medical device (IMD) 10. The IMD 10 includes a conductive housing 11, a connector block 12, an atrial lead 15, a ventricular lead 16 coupled to the connector block 12.

The lead connectors 13, 14, 18 and 22 are inserted into the connector block 12, which contains corresponding electrical connectors for coupling to the various connector rings and pins. Optionally, insulation of the outward facing portion of the housing 11 of the IMD 10 may be provided in the form of a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used in conjunction with one or both of the coiled electrodes 20, 28.

The ventricular lead 16 includes an elongated insulative lead body 16 carrying four mutually insulated conductors. The ventricular lead 16 includes a number of components including electrical unipolar lead connectors 14, 18, 22, elongated insulative lead body 16, extendable helix electrode 26, elongated coil electrodes 20, 28, a ring electrode 24, and an insulative electrode head 27. Electrical lead connector 14 is an in-line bipolar connector carrying a connector ring and a connector pin, coupled to the ring electrode 24 and the extendable helix electrode 26, respectively. Located on the lead body 16 are a ring electrode 24, an extendable helix electrode 26, mounted retractably within an insulative electrode head 27, and elongated coil electrodes 20 and 28. Each of the electrodes is coupled to one of the coiled conductors within the lead body 16. The ring electrode 24 and the extendable helix electrode 26 are employed for cardiac pacing and for sensing ventricular depolarizations. At the proximal end of the lead body 16 are two unipolar connectors 18 and 22 which each carry a connector pin coupled to one of the coiled electrodes 20 and 28. Coiled electrodes 20 and 28 are employed in conjunction with the conductive housing 11 of the IMD 10 for delivery of ventricular cardioversion and defibrillation pulses.

The atrial lead 15 includes a number of components including an in-line lead connector 13, elongated insulative lead body 15, extendable helix electrode 17, an insulative electrode head 19, and a ring electrode 21. The atrial lead 15 is illustrated as a conventional bipolar atrial pacing lead 15. At the proximal end of the lead is an in-line connector 13 which carries a connector ring and a connector pin, coupled to electrodes 21 and 17, respectively. In alternative lead systems, a defibrillation electrode, for example corresponding to electrode 28, might instead be mounted to the atrial lead, or might be mounted to a coronary sinus lead, for location in the coronary sinus and great cardiac vein. The atrial lead 15 includes an elongated insulative lead body 15, carrying two concentric coiled conductors, separated from one another by tubular insulative sheaths. Located adjacent the J-shaped distal end of the lead are the ring electrode 21 and the extendable helix electrode 17, mounted retractably within an insulative electrode head 19. Each of the electrodes is coupled to one of the coiled conductors within the lead body 15. The extendable helix electrode 17 and the ring electrode 21 are employed for atrial pacing and for sensing atrial depolarizations.

Figure 2:
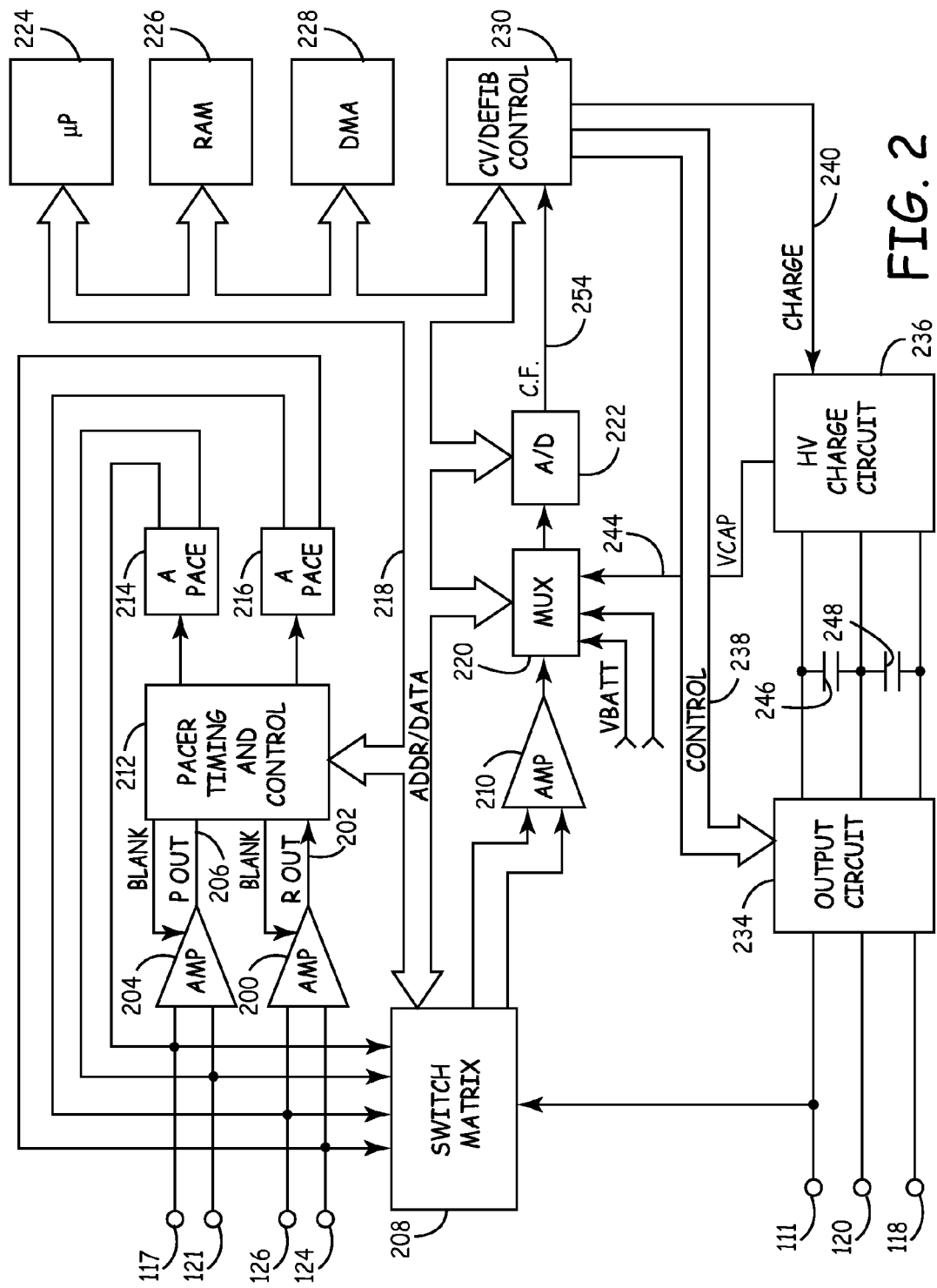
FIG. 2 is a functional schematic diagram of an implantable medical device (IMD) in which the present invention may be implemented.

FIG. 2 is a functional schematic diagram of an implantable medical device (IMD) in which the present invention may be implemented. In this implementation, the IMD can be an implantable pacemaker/cardioverter/defibrillator device. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 111 corresponds to electrode 11, and is the uninsulated portion of the housing of the IMD. Electrode 120 corresponds to electrode 20 and is a defibrillation electrode located in the right ventricle. Electrode 118 corresponds to electrode 28 and is a defibrillation electrode located in the superior vena cava. Electrodes 124 and 126 correspond to electrodes 24 and 26, and are used for sensing and pacing in the ventricle. Electrodes 117 and 121 correspond to electrodes 17 and 21 and are used for pacing and sensing in the atrium.

Electrodes 111, 118 and 120 are coupled to high voltage output circuit 234. Electrodes 124 and 126 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 124 and 126 exceeds the present sensing threshold.

Electrodes 117 and 121 are located on or in the atrium and are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 117 and 121 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 117, 121, 124 and 126. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 4,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern IMDs, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al., each of which is incorporated by reference in its entirety.

Tachyarrhythmia Detection, Classification and Therapy

Figure 3A:
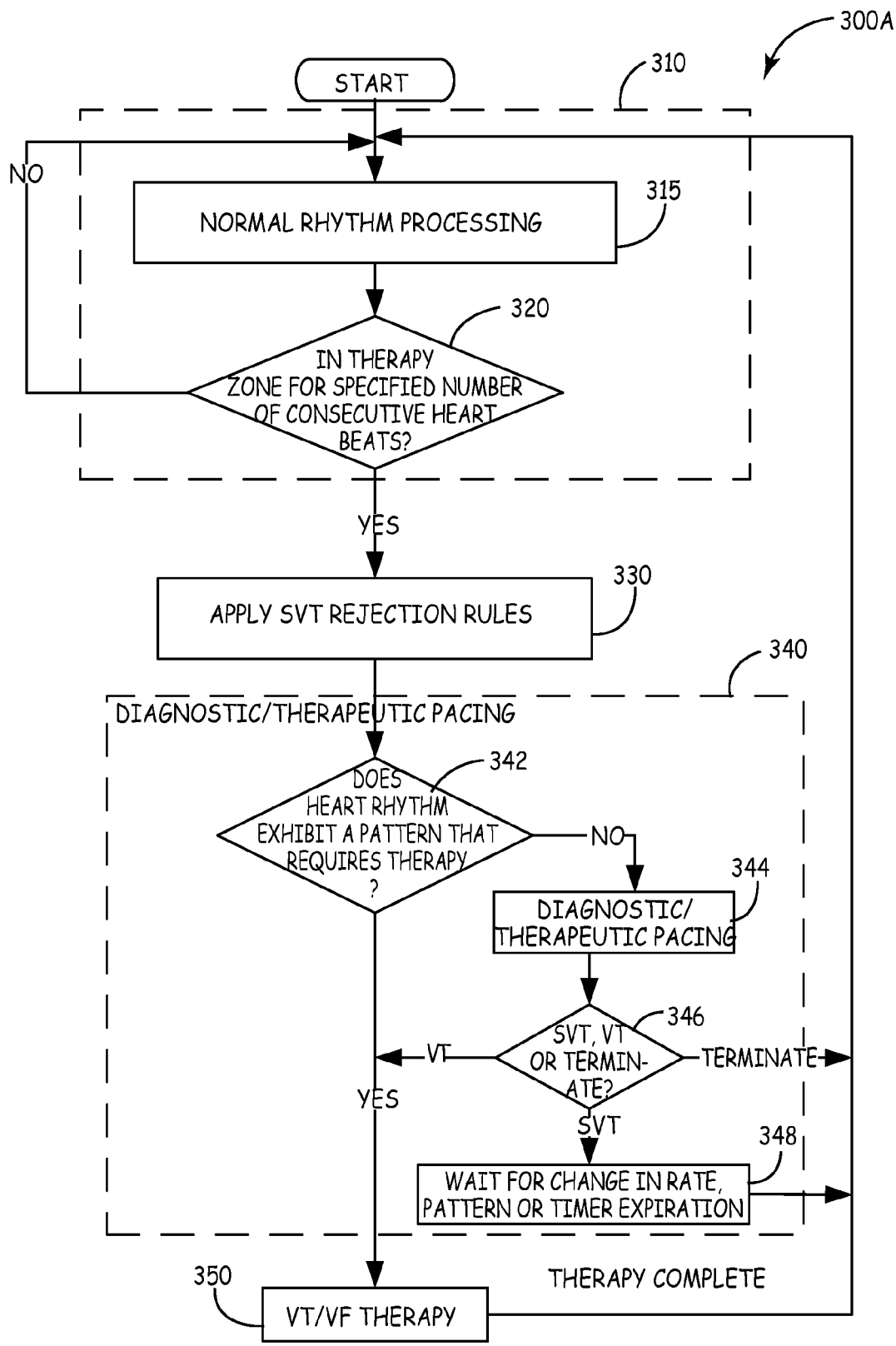
FIG. 3A is a flow chart which illustrates a tachyarrhythmia detection, classification and therapy method according to an exemplary embodiment of the present invention.

FIG. 3A is a flow chart which illustrates a tachyarrhythmia detection, classification and therapy method 300A according to an exemplary embodiment of the present invention. It should be noted that in many IMDs, a physician or other health care professional programs the IMD (before method 300A is initiated) to set a threshold heart rate (THR) and a detection beat threshold (DBT) which can be defined as a specified number of consecutive heart beats (SNCHBs). The THR is set on a patient-by-patient basis, where the particular THR is set to establish a general baseline between fast heart rhythms that may not require treatment (e.g., AF, AVNRT, ST) versus other fast heart rhythms that might (i.e., may or do) require treatment (e.g., AT, SVT, VT, VF) for that particular patient. The SNCHBs is a number of consecutive beats that a measured instantaneous heart rate (IHR) must be greater than or equal to the THR before the measured IHR is to be considered for treatment or therapy.

Normal Rhythm Processing

Method 300A begins at block 310. At block 310, the IMD is performing normal rhythm processing (step 315), and at step 320, the IMD determines whether the patient's heart rhythm remains in a "therapy zone" for a specified number of consecutive heart beats. One exemplary implementation of steps 315 and 320 will now be described. Leads in the patient's heart sense/determine when electrical events or "depolarizations" happen, and based on this information, the IMD can determine an instantaneous heart beat rate (IHR). The IMD performs normal rhythm processing (step 315) while the IHR is below the THR. When the IHR exceeds (i.e., greater than or equal to) the THR, then the patient may be experiencing a tachyarrhythmia. The method 300A then proceeds to step 320. Step 320 is performed to help ensure that the IHR is indicative of a tachyarrhythmia that warrants treatment before treating it. In this implementation of step 320, the IMD starts a counter that counts the number of SNCHBs during which the IHR is greater than or equal to the THR to determine whether the patient's IHR remains in a range indicative of a tachyarrhythmia for a SNCHBs. In such implementations, if the IHR falls below the THR before the SNCHBs, then the IHR is considered to be "safe" and the method 300A returns to step 315 where the IMD continues to monitor/measure the IHR. In some situations a fast IHR may terminate by itself without therapy (e.g., the IHR may generate a few short fast runs), and it is appropriate to "wait and see" if the IHR exceeds the THR for an extended number of beats.

Although IHR is an important factor to consider in distinguishing between fast heart rhythms that do not require treatment (e.g., AF, AVNRT, ST) and other fast heart rhythms that might (i.e., may or do) require treatment (e.g., AT, SVT, VT, VF), using IHR as the only criteria to make this distinction achieves limited success since there can be an overlap between fast heart rhythms that do not require treatment and other fast heart rhythms that might require treatment. For example, in some cases such as when a patient is excited or is physically exerting herself, the IHR may exceed the THR even though the IHR is does not necessarily need to be treated (e.g., is likely to self-correct without therapy).

To improve the detection algorithm's ability to distinguish between irregular heart events and those which should be treated, at step 330, supplemental passive detection criteria other than IHR information can be examined before proceeding to diagnostic/therapeutic pacing at step 340 or starting VT/VF therapy at step 350. This allows events which should be treated with therapy to be distinguished from other events which do not need to be treated. In short, step 330 allows the IMD to examine certain criteria which would not necessarily benefit from ventricular therapies, before applying therapy.

SVT Rejection Rules

When the patient's heart rhythm remains in a "therapy zone" for a specified number of consecutive heart beats, the method 300A proceeds to step 330, where SVT rejection rules are applied by the IMD. SVT rejection rules refer to a set of rules which are used to detect and classify arrhythmias of the heart and to deliver appropriate therapy. The IMD classifies arrhythmias based on a set of prioritized rules, each of the rules defining a plurality of criteria based upon characteristics of sensed depolarizations of heart tissue, each rule being met when the criteria associated with the rule are met. Some rules, when met, trigger delivery of anti-arrhythmia therapy. Other rules, when met, inhibit delivery of anti-arrhythmia therapy. The rules may be met simultaneously, and if so, the highest priority rule governs the behavior of the device. Examples of SVT rejection rules are described, for example, in commonly assigned U.S. Pat. Nos. 6,731,978, 6,487,443, 6,259,947, 6,141,581, 5,991,656, 5,855,593, and 5,545,186 issued to Olson et al., which are incorporated by reference herein in their entirety. During application of the SVT rejection rules, among other things, the IMD examines one or more SVT rejection rules to help differentiate between fast heart rhythms that do not require treatment (e.g., AF, AVNRT, ST), and other fast heart rhythms that might require treatment (e.g., AT, SVT, VT, VF).

As described in the Olson patents, the SVT rejection/detection rules are employed to identify the various rhythm types listed above and to withhold delivery of therapy when appropriate. The SVT rejection/detection rules can include, for example, a VF Rule, a VT+SVT Rule, a monomorphic VT Rule, an Atrial fibrillation (AF) rule, an Atrial Flutter rule, a Sinus Tachycardia (ST) Rule, a AVNRT Rule, and a NSR Rule. Of these rules, the AF/A Flutter rules, the ST rule, and the AVNRT rule and the NSR rule all help to distinguish heart rhythms that do not require ventricular therapy. Other rules help to distinguish heart rhythms that might require ventricular therapy (e.g., VF or VT) In addition, other rules not included in this list (such as an electrogram morphology rule) can be implemented to help identify the various rhythm types and to withhold delivery of ventricular therapy. The particular combination of SVT rejection rules that are applied or examined can vary depending on the implementation, but in general, each of the SVT rejection rules that are implemented must be satisfied before proceeding to diagnostic/therapeutic pacing at step 340 and/or starting VT/VF therapy at step 350.

When the IMD determines that the patient's heart rhythm meets or satisfies some of the SVT rejection rules which indicate that a fast heart rhythm is occurring that might (i.e., may or does) require treatment (e.g., VT, VF), and the method 300A proceeds to step 340, where the IMD performs diagnostic/therapeutic pacing to further discriminate between SVT type rhythms and VT type rhythms, and then takes appropriate action including diagnostic/therapeutic pacing (at step 344) and/or VT/VF therapy (at step 350). In one implementation, the diagnostic/therapeutic pacing performed at step 340 can be viewed as an additional SVT rejection rule, and in this regard, step 340 could be implemented as one of the SVT rejection rules within step 330.

Diagnostic/Therapeutic Pacing

In this implementation, the diagnostic/therapeutic pacing method 340 begins at step 342, where the IMD examines supplemental criteria to determine whether the heart rhythm exhibits a pattern that represents a dangerous condition and therefore requires VT/VF therapy. In some embodiments of step 342, the IMD determines whether the heart rhythm exhibits a pattern of atrial events and ventricular events that may require VT/VF therapy. In one implementation of this embodiment of step 342, the IMD determines whether the number of atrial events is greater than, substantially equal to, or less than the number of ventricular events. When the number of atrial events is substantially equal to the number of ventricular events (i.e., pattern or ratio of atrial events and ventricular events is approximately the same or one-to-one (1.1)), then the IMD determines that the heart rhythm is consistent with one of several types of tachyarrhythmias including sinus tachycardia (ST), atrial tachycardia (AT), atrial ventricular nodal reentrant tachycardia (AVNRT), atrial ventricular reentrant tachycardia (AVRT), and ventricular tachycardia (VT) with 1:1 retrograde conduction. If the IMD determines, at step 342, that the heart rhythm exhibits a pattern that requires VT/VF therapy, then the method 300A proceeds to step 350 where VT/VF therapy begins and continues until complete, at which point the method 300A proceeds to step 315.

When the number of atrial events is less than the number of ventricular events (i.e., ratio of atrial events to ventricular events is one-to-N (1:N)), then the IMD determines that the heart rhythm is ventricular in origin and will require therapy. When the number of atrial events is greater than the number of ventricular events (i.e., ratio of atrial events to ventricular events is N-to-one (N:1)), then the IMD determines that the heart rhythm is consistent with one of several types of tachyarrhythmias including atrial fibrillation, atrial flutter or double tachycardia (i.e., simultaneous AF and VT/VF).

If the IMD determines, at step 342, that the heart rhythm exhibits a pattern that does not necessarily require VT/VF therapy, then the method 300A proceeds to step 344, where the IMD begins a diagnostic/therapeutic pacing sequence. The IMD applies or delivers a diagnostic/therapeutic pacing sequence to the atrium and/or ventricle in an attempt to control or correct the heart rate and/or possibly stop the tachyarrhythmia. To apply the pacing sequence, the IMD generates a series of electrical pulses or shocks which are sent via the leads to the atrium and ventricle to drive those chambers of the heart to beat in accordance with a particular beat sequence.

As used herein, the term "diagnostic/therapeutic pacing sequence," refers to a pacing sequence delivered to the heart for a diagnostic and/or therapeutic purpose. In other words, the purpose of the diagnostic/therapeutic pacing sequence is to either aid in discriminating between these different rhythms (e.g., diagnosing the rhythm as AT/SVT or VT/VF) and/or to control or correct the heart rate and/or possibly terminate the tachycardia. In contrast to an anti-tachycardia pacing (ATP) sequence (also referred to herein as VT/VF therapy) that is delivered to the heart for the purpose of terminating a tachycardia, a diagnostic/therapeutic pacing sequence refers to a broader set of pacing strategies that in some cases may resemble an anti-tachycardia pacing (ATP) sequence (i.e., VT/VF therapy) often used to terminate VT/VF, but which can also vary in terms of frequency of pacing pulses and/or the location of delivery. For instance, a diagnostic/therapeutic pacing sequence could also be single extra stimuli, could be delivered into both the atrium and the ventricle simultaneously or sequentially first in one chamber and then the other.

At step 346, the IMD determines the response of the patient's heart to the diagnostic/therapeutic pacing sequence. In particular, the IMD determines whether the diagnostic/therapeutic pacing sequence terminated the tachyarrhythmia, and if not, whether the patient's heart rhythm is indicative of a supraventricular tachycardia (SVT) type rhythm or a ventricular tachycardia (VT) type rhythm.

When the IMD determines that the patient's heart rhythm following the diagnostic/therapeutic pacing sequence is indicative that the tachyarrhythmia has terminated, method 300A loops back to step 315, where the IMD performs normal rhythm processing.

When the IMD determines that the patient's heart rhythm following the diagnostic/therapeutic pacing sequence is indicative of a supraventricular tachycardia (SVT) type rhythm, then the method 300A proceeds to step 348, where the IMD waits for a trigger event which indicates that the originally diagnosed rhythm has changed and is to be re-evaluated. In one implementation, trigger events can be a change in one or more of the patient's heart beat rate, heart beat pattern, or the expiration of a timer. When one of these trigger events occurs, the method 300A loops back to step 315, where the IMD performs normal rhythm processing.

When the IMD determines that the patient's heart rhythm following the diagnostic/therapeutic pacing sequence is indicative of a ventricular tachycardia (VT) type rhythm, then the method 300A proceeds to step 350, where the IMD starts a VT/VF therapy sequence. Once the VT/VF therapy sequence is complete, the method 300A loops back to step 315, where the IMD performs normal rhythm processing.

Figure 3B:
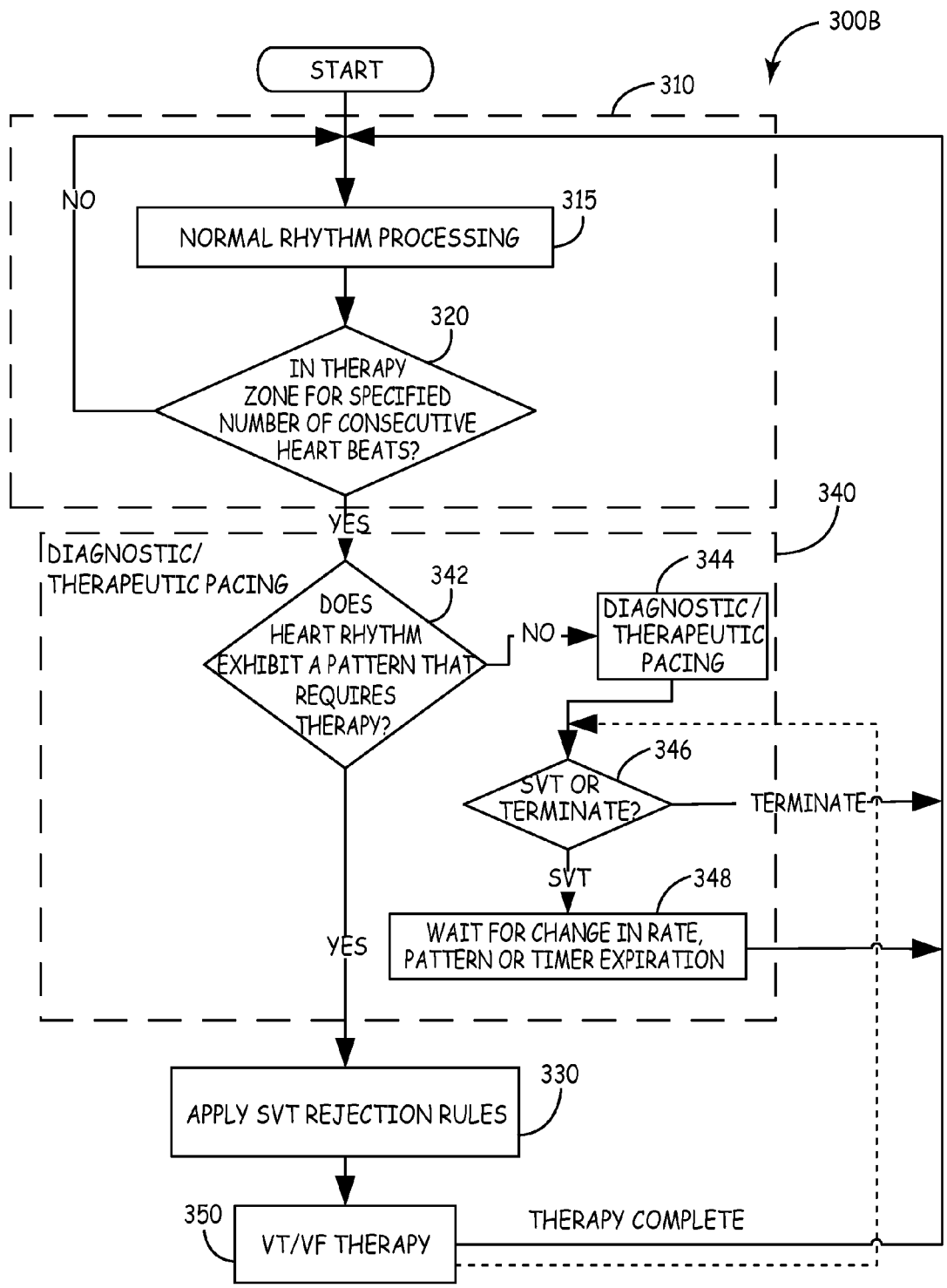
FIG. 3B is a flow chart which illustrates a tachyarrhythmia detection, classification and therapy method according to other exemplary embodiments of the present invention.

FIG. 3B is a flow chart which illustrates a generic tachyarrhythmia detection and therapy method 300A according to other exemplary embodiments of the present invention. The embodiments illustrated in FIG. 3B comprise the same general steps illustrated in FIG. 3A, and therefore for purposes of brevity the details of those steps will not be described again, and only the differences between FIG. 3A and 3B will be described below. In FIG. 3B, following step 320, the method 300B proceeds to step 340, where the IMD performs diagnostic/therapeutic pacing prior to applying SVT rejection rules at step 330.

Diagnostic/Therapeutic Pacing

When the patient's heart rhythm remains in a "therapy zone" for a specified number of consecutive heart beats, the method 300B proceeds to step 340, where the IMD performs diagnostic/therapeutic pacing to further discriminate between SVT type rhythms and VT type rhythms, and then takes appropriate action including diagnostic therapy (at step 344). As described above, the diagnostic/therapeutic pacing method 340 begins at step 342, where the IMD examines supplemental criteria to determine whether the heart rhythm exhibits a pattern that represents a dangerous condition and therefore requires VT/VF therapy. When the IMD determines, at step 342, that the heart rhythm exhibits a pattern that requires VT/VF therapy, then the method 300B proceeds to step 330. On the other hand, when the IMD determines, at step 342, that the heart rhythm exhibits a pattern that does not necessarily require VT/VF therapy, then the method 300B proceeds to step 344, where the IMD begins a diagnostic/therapeutic pacing sequence, as described above, and at step 346, the IMD determines the response of the patient's heart to the diagnostic/therapeutic pacing sequence. In particular, the IMD determines whether the diagnostic/therapeutic pacing sequence terminated the tachyarrhythmia, and if not, whether the patient's heart rhythm is indicative of a supraventricular tachycardia (SVT) type rhythm or a ventricular tachycardia (VT) type rhythm. When the IMD determines that the patient's heart rhythm following the diagnostic/therapeutic pacing sequence has terminated the tachyarrhythmia, method 300B loops back to step 315, where the IMD performs normal rhythm processing. When the IMD determines that the patient's heart rhythm following the diagnostic/therapeutic pacing sequence is indicative of a supraventricular tachycardia (SVT) type rhythm, then the method 300B proceeds to step 348, where the IMD waits for a trigger event which indicates that the originally diagnosed rhythm has changed and is to be re-evaluated. In one implementation, trigger events can be a change in one or more of the patient's heart rate, heart beat pattern, or the expiration of a timer. When one of these trigger events occurs, the method 300B loops back to step 315, where the IMD performs normal rhythm processing. When the IMD determines that the patient's heart rhythm following the diagnostic/therapeutic pacing sequence is indicative of a ventricular tachycardia (VT) type rhythm, then the method 300B proceeds to step 330.

Supraventricular Tachycardia (SVT) Rejection Rules

Before beginning VT/VF therapy at step 350, the IMD applies SVT rejection rules at step 330 to examine supplemental passive detection criteria to rule out events which would not necessarily benefit from VT/VF therapies.

When the IMD determines, based on the SVT rejection rules applied at step 330, that the patient's heart rhythm is potentially dangerous, and the method 300B proceeds to step 350, where the IMD begins VT/VF therapy and continues until complete.

In one implementation of method 300B, when the VT/VF therapy sequence is complete, the method 300B loops back to step 315, where the IMD performs normal rhythm processing.

In another implementation of method 300B, when the VT/VF therapy sequence is complete, the method 300B loops back to step 346, where the IMD "re-enters" the diagnostic/therapeutic pacing method 340, where the IMD determines the response of the patient's heart to the VT/VF therapy. In particular, the IMD determines whether the VT/VF therapy terminated the tachyarrhythmia, and if not, whether the patient's heart rhythm is indicative of a supraventricular tachycardia (SVT) type rhythm or a ventricular tachycardia (VT) type rhythm. This allows for a more complete integration of detection and therapy processing and for terminating therapy once a potentially dangerous tachycardia has been terminated.

The diagnostic/therapeutic pacing techniques described above represent one exemplary implementation. Another exemplary implementation of a diagnostic/therapeutic pacing technique will now be described with reference to FIGS. 4-7.

Exemplary Diagnostic/Therapeutic Pacing Method

Figure 4:
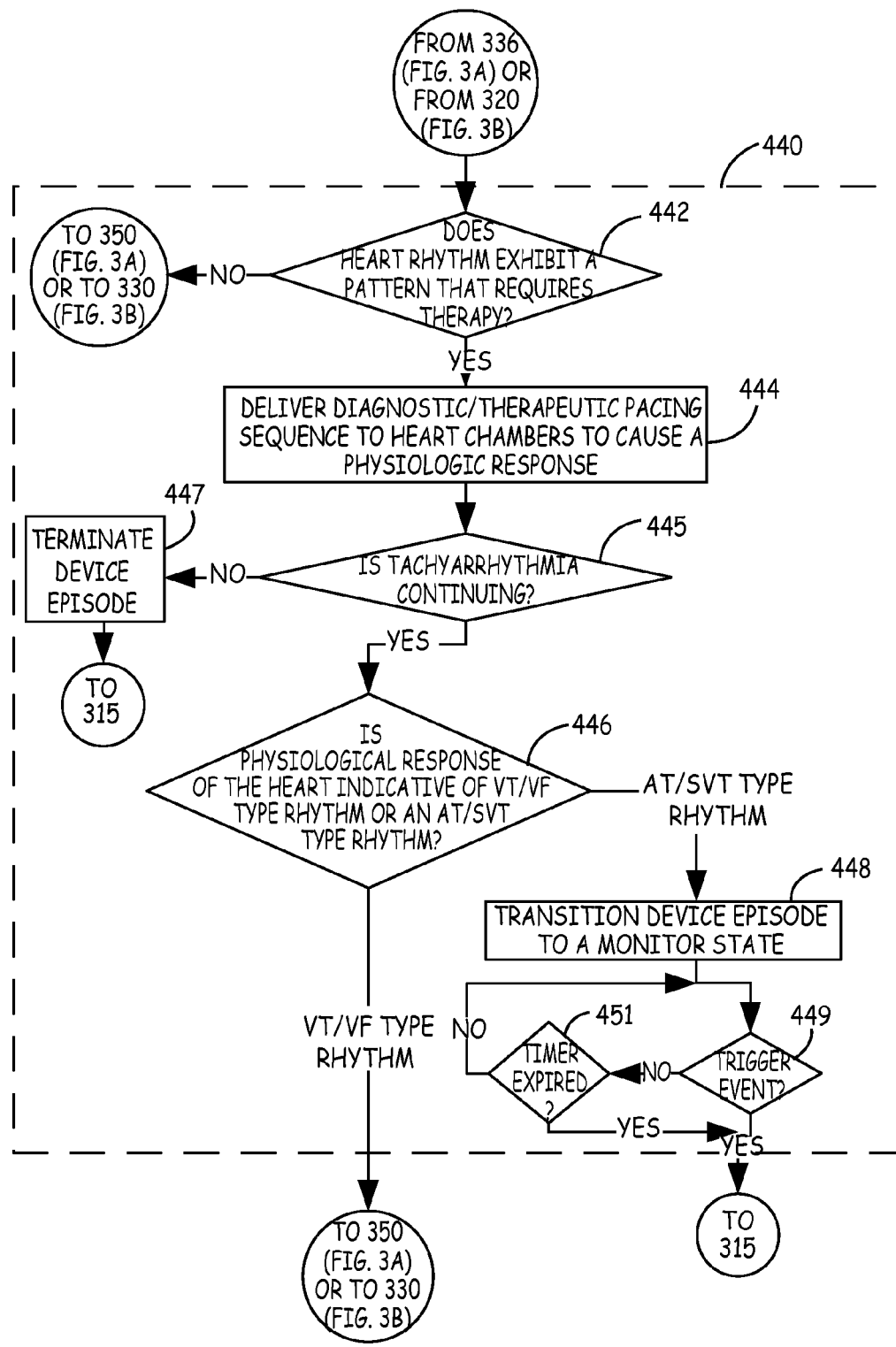
FIG. 4 is a flow chart which illustrates a diagnostic/therapeutic pacing method (DDM) for use in a tachyarrhythmia detection, classification and therapy methods of FIGS. 3A and 3B according to an exemplary embodiment of the present invention.

FIG. 4 is a flow chart which illustrates a diagnostic/therapeutic pacing method (DDM) 440 for use in tachyarrhythmia detection, classification and treatment methods 300A, 300B of FIGS. 3A and 3B according to an exemplary embodiment of the present invention. The DDM 440 can be used in an IMD to distinguish between fast heart rhythms which should not be treated, and potentially dangerous fast heart rhythms which should be treated.

At step 442, the IMD examines supplemental criteria to determine whether the heart rhythm exhibits a pattern that represents a dangerous condition and therefore requires VT/VF therapy If the IMD determines, at step 442, that the heart rhythm exhibits a pattern that requires VT/VF therapy, then the method 440 either proceeds to step 350 of FIG. 3A or step 330 of FIG. 3B, as described above.

If the IMD determines, at step 442, that the heart rhythm exhibits a pattern that does not necessarily require VT/VF therapy, then the method 440 proceeds to step 444, where the IMD delivers a diagnostic/therapeutic pacing sequence to the atrium and/or ventricle to cause a physiologic response. In one implementation, the IMD delivers the diagnostic/therapeutic pacing sequence of electrical pulse(s) or other stimuli to either an atrium or to a ventricle of the patient's heart in an attempt to synchronize the beating of those chambers. In another implementation, the IMD simultaneously delivers the diagnostic/therapeutic pacing sequence of electrical pulse(s) or other stimuli to an atrium and to a ventricle of the patient's heart in an attempt to synchronize the beating of those chambers. The diagnostic/therapeutic pacing sequence is designed to overdrive the beat rate of at least one chamber (or both chambers) at a rate faster than the intrinsic beat rate to thereby synchronize the contractions or "beat rhythm" of the atrium and the ventricle that are being monitored. In some patients, when the diagnostic/therapeutic pacing sequence stops, the tachyarrhythmia may be terminated in which case normal rhythm processing resumes at step 315, or the tachyarrhythmia may continue with the chamber responsible for the tachyarrhythmia exhibiting the first post-pacing intrinsic activity.

At step 445, the IMD determines whether the tachyarrhythmia continues after the diagnostic/therapeutic pacing sequence is applied to the atrium and the ventricle. In one implementation, eight consecutive ventricular cycles longer than the THR is evidence that the tachyarrhythmia has terminated.

If the IMD determines that the tachyarrhythmia is no longer continuing after the pacing sequence is applied, then the DDM 440 proceeds to step 447, where the device episode is terminated, and the DDM 440 then proceeds to step 315 of FIG. 3A or 3B. For instance, in one implementation, the DDM 440 instructs therapy module relinquish control and stop therapy.

By contrast, when the IMD determines that the tachyarrhythmia is continuing, the method proceeds to step 446, where the IMD continues to monitor and analyze the subsequent physiologic response of the heart to determine which chamber of the heart is responsible for causing the tachyarrhythmia.

In one implementation of step 446, based on the physiologic response (i.e., the beat rhythm of the atrium and the ventricle) of the heart in response to the pacing sequence, the IMD determines which one of those chambers responds first with an electrical event, and based on this information, the IMD can determine whether the tachyarrhythmia is indicative of a VT/VF type rhythm or a SVT type rhythm. In one embodiment, the chamber (i.e., the atrium or the ventricle) which responds first with an event can be deemed to be the cause or source of the accelerated beat which is causing the tachyarrhythmia.

Figure 5:
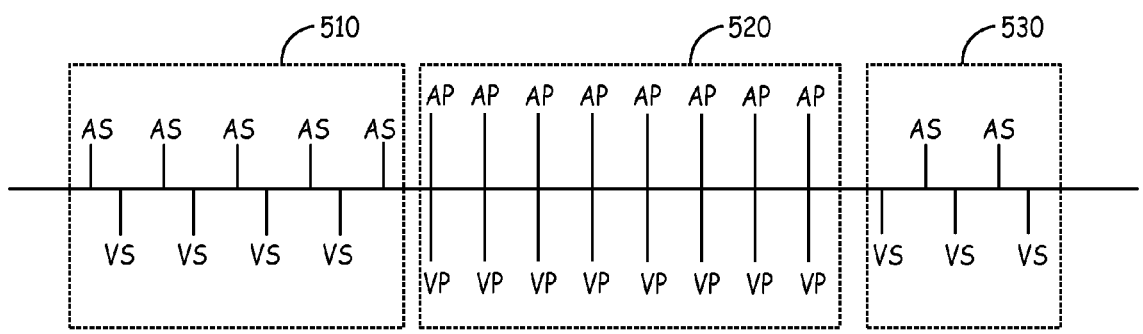
FIG. 5 is a timing diagram that illustrates a series of sensed events (AS, VS) followed by a series of paced events (AP, VP) followed by another series of sensed events (VS, AS)

For example, in one exemplary implementation, when the IMD senses a ventricular event first after the atrium and/or ventricle are no longer paced, as illustrated in FIG. 5 (described below), then the ventricle is deemed to be the chamber of origin (e.g., cause or source) of the accelerated beat which is causing the tachyarrhythmia. The tachyarrhythmia is deemed to be a potentially dangerous VT type rhythm or a VF type rhythm. FIG. 5 is a timing diagram 500 that illustrates a series of sensed events (AS, VS) 510 followed by a series of paced events (AP, VP) 520 followed by another series of leading sensed events (VS, AS) 530. In one implementation, the IMD monitors the response of the heart by analyzing events over time to determine if the tachyarrhythmia is continuing. To explain further, each time the heart beats or contracts, there is an associated electrical event or "depolarization," and leads placed inside the heart can be used to pick up information about the electrical event, and send this information to sensing/detection algorithms, which run on a processor in the IMD, that can sense when the electrical event happens. In one implementation, each occurrence of these electrical cardiac events can be expressed as sensed events or paced events such as: atrial paced (AP) events, ventricular paced (VP) events, ventricular sensed (VS) events and atrial sensed (AS) events. As used herein, an AP event refers to a paced atrial event (e.g., that the atrium is either preparing to contract or is contracting in response to a pacing stimulus or stimuli). As used herein, a VP event refers to a paced ventricular event (e.g., that the ventricle is either preparing to contract or is contracting in response to a pacing stimulus or stimuli). As used herein, an AS event refers to an intrinsic atrial event (e.g., that the atrium is either preparing to contract or contracting naturally at its own intrinsic rate without being subjected to pacing). As used herein, a VS event refers to an intrinsic ventricular event (e.g., that the ventricle is either preparing to contract or contracting naturally at its own intrinsic rate without being subjected to pacing). The beat rhythm of the atrium and the ventricle are synchronized when the AP events and the VP events are occurring at approximately the same time, and have a one-to-one (or an approximately one-to-one) relationship or "beat rhythm."

As illustrated in block 510 of FIG. 5, the series of sensed events (AS, VS) 510 begins with an atrial sensed (AS) event followed by a ventricular sensed (VS) event. A pattern resumes in which the AS events lead VS events by an amount of time. The pattern illustrated in block 510 is consistent with one of a sinus tachyarrhythmia (ST), an atrial tachyarrhythmia (AT), an AV nodal reentrant tachyarrhythmia (AVNRT) or a ventricular tachyarrhythmia (VT) with 1:1 retrograde conduction. Following block 510, pacing of the atrium and ventricle begins, and at block 520, a series of simultaneous atrial paced (AP) events and ventricular paced (VP) events begins and continues for a time period (in block 520) during which the atrial paced (AP) events and ventricular paced (VP) events continue in synchronization with each other as the atrium and ventricle are being paced. Just before block 530, the pacing of the atrium and/or ventricle stops. In this particular timing diagram, at block 530, the first post-pace intrinsic event is a ventricular sensed (VS) event, which in most cases indicates that the ventricle is deemed to be the chamber of origin (e.g., cause or source) of the accelerated heart rate that is causing the tachycardia. Therefore, in most cases it can be assumed that the tachycardia has a rhythm indicative of a VT type rhythm or a VF type rhythm.

Figure 6:
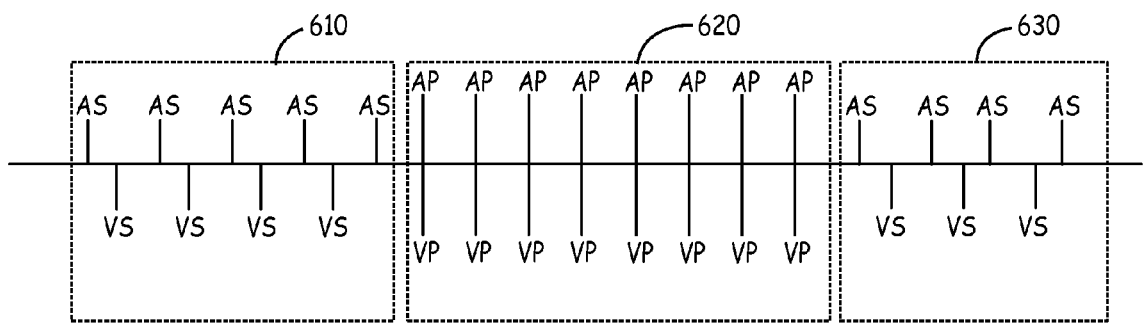
FIG. 6 is a timing diagram that illustrates a series of sensed events (AS, VS) followed by a series of paced events (AP, VP) followed by another series of sensed events (AS, VS)

By contrast, if the detection algorithm senses an AS event first after the atrium and/or ventricle stop being paced, as illustrated in FIG. 6 (described below), then the atrium (or some entity above the ventricle) is deemed to be the chamber of origin (e.g., cause or source) of the accelerated heart rhythm. The tachyarrhythmia is deemed to be a atrial or supraventricular tachycardia (AT/SVT) type rhythm. FIG. 6 is a timing diagram 600 that illustrates a series of sensed events (AS, VS) 610 followed by a series of paced events (AP, VP) 620 followed by another series of sensed events (AS, VS) 630. As illustrated in block 610 of FIG. 6, the series of sensed events (AS, VS) 610 begins with an atrial sensed (AS) event followed by a ventricular sensed (VS) event in a pattern which continues within block 610. The PR pattern illustrated in block 610 is consistent with one of a sinus tachyarrhythmia (ST), an atrial tachyarrhythmia (AT), an AV nodal reentrant tachyarrhythmia (AVNRT) or a ventricular tachyarrhythmia (VT) with 1:1 retrograde conduction. Following block 610, pacing of the atrium and ventricle begins. At block 620, a series of simultaneous atrial paced (AP) events and ventricular paced (VP) events begins and continues for a time period in block 620 such that the atrial paced (AP) events and ventricular paced (VP) events continue for a pre-determined period of time. Just before block 630, application of the pacing sequence stops (and pacing of the atrium and ventricle stop). In this particular timing diagram 600, at block 630, the first post-pace intrinsic event, after the atrium and ventricle stop being paced, happens to be an atrial sensed (AS) event. In most cases this indicates that the atrium (or something above the ventricle) is the cause or source of the accelerated rhythm, and therefore, in most cases it can be assumed that the post-pace intrinsic rhythm is indicative of a supraventricular tachycardia (SVT) type rhythm.

Referring again to FIG. 4, when IMD determines at step 446 that the tachyarrhythmia is indicative of a VT-type rhythm or VF-type rhythm, then the DDM 440 proceeds to step 350 of FIG. 3A or to step 330 of FIG. 3B.

When IMD determines that the tachyarrhythmia is indicative of either an atrial tachycardia (AT) type rhythm or a supraventricular tachycardia (SVT) type rhythm, then the DDM 440 proceeds to step 448, where the DDM 440 transitions to a monitor state. While in the monitoring state, the IMD continues to monitor the pattern of atrial and ventricular events for a trigger event at step 449. Trigger events indicate that the originally diagnosed rhythm has changed and is to be re-evaluated. Trigger events can include, for example, a change in the pattern of atrial and ventricular events (or tachyarrhythmia AV pattern), a change in morphology, a change in the heart rate, etc.).

At step 451, the IMD can determine whether a timer has expired for detecting a trigger event. If the timer has not expired, the DMM 440 loops back to step 449 where the IMD continues to monitor for a trigger event. If a trigger event occurs or if the timer expires (i.e., no trigger event occurs within the time period), then the process loops back to step 315 of FIG. 3.

Other Enhancements

As noted above, when the IMD determines that the tachyarrhythmia is continuing at step 430 (i.e., that that therapy was not successful and the diagnostic/therapeutic pacing sequence did not terminate the tachycardia), then the IMD operating according to the DDM 440 continues to monitor and analyze the subsequent physiologic response of the heart (i.e., the beat rhythms of the atrium and the ventricle) to determine or predict which chamber of the heart is responsible for causing the tachyarrhythmia. One technique for doing so will now be described with reference to FIG. 7.

Figure 7:
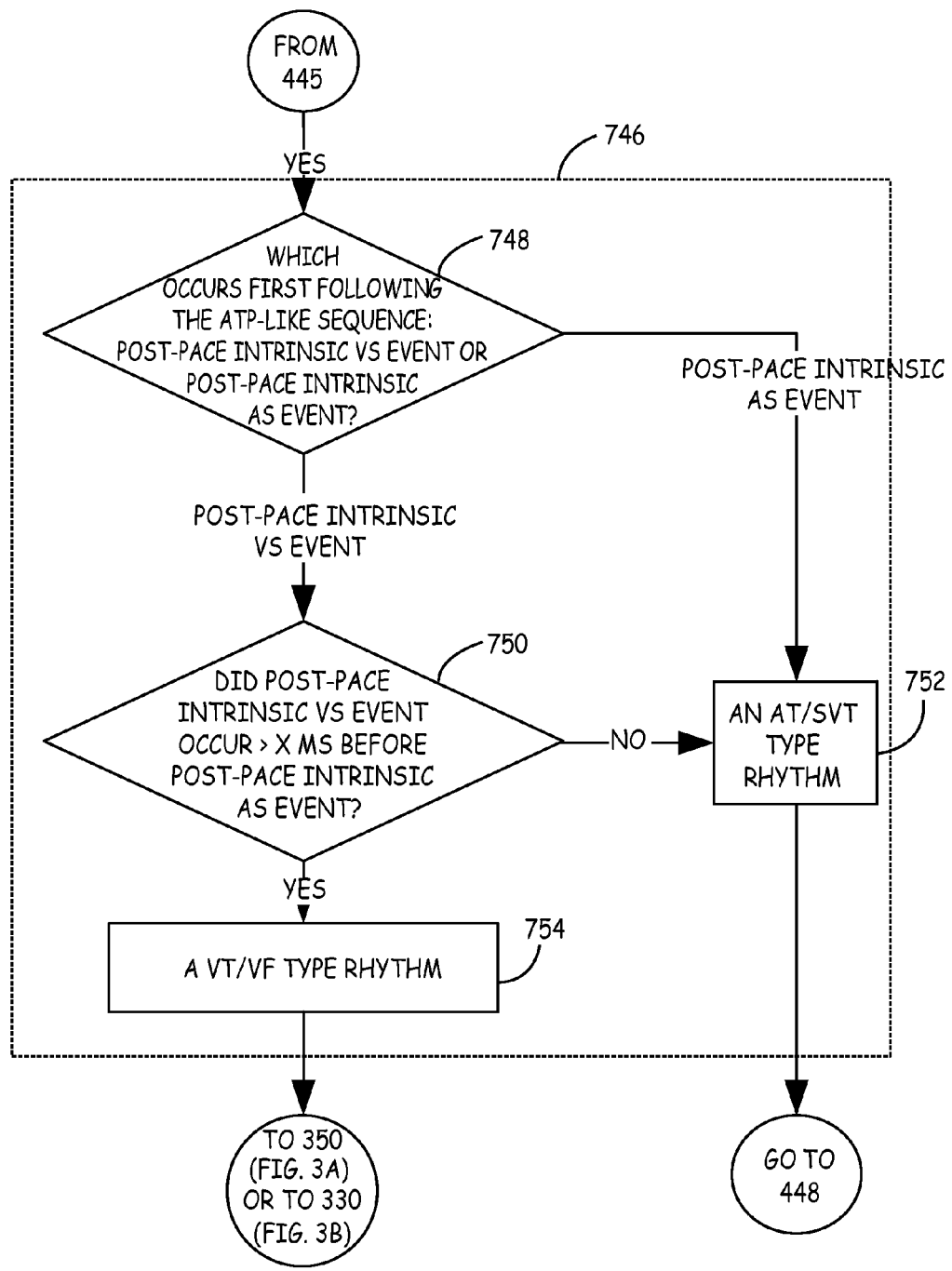
FIG. 7 is a flow chart which illustrates a method for determining whether a tachyarrhythmia is indicative of an atrial tachycardia (AT)/supraventricular tachycardia (SVT) type rhythm or is indicative of a ventricular tachycardia (VT)/ventricular fibrillation (VF) type rhythm according to an exemplary implementation of the present invention.

FIG. 7 is a flow chart which illustrates a method 746 for determining whether a tachyarrhythmia is indicative of an atrial tachycardia (AT)/supraventricular tachycardia (SVT) type rhythm or is indicative of a ventricular tachycardia (VT)/ventricular fibrillation (VF) type rhythm according to an exemplary implementation of the present invention.

At step 748, the IMD operating according to the method 746 determines whether a post-pace intrinsic ventricular sensed (VS) event or a post-pace intrinsic atrial sensed (AS) event occurs first following stoppage of the pacing. By making this determination, the IMD can roughly determine which chamber (i.e., the atrium or the ventricle) responds first with an electrical event (an AS event or VS event), and thus whether the tachyarrhythmia is generally indicative of a VT/VF type rhythm or an AT/SVT type rhythm. In general, the chamber (i.e., the atrium or the ventricle) which responds first with an event (AS event or VS event) can be deemed to be the cause or source of the accelerated beat or tachyarrhythmia. However, in some cases patterns which tend to indicate the VT/VF and the AT/SVT type rhythms can overlap somewhat, and therefore it is desirable to consider other criteria before making the determination as to whether the tachyarrhythmia is generally indicative of a VT/VF type rhythm or an AT/SVT type rhythm.

When a post-pace intrinsic AS event occurs first following the pacing sequence, then the method 738 proceeds from step 748 to step 752, where an AT/SVT type rhythm is detected. In other words, when an AS event occurs first following the diagnositic/therapeutic pacing, as illustrated in FIG. 6, then the atrium (or some entity above the ventricle) is deemed to be the chamber of origin (e.g., cause or source) of the accelerated rhythm, and the tachyarrhythmia is deemed to be an atrial or supraventricular tachycardia (AT/SVT) type rhythm. The method 746 then proceeds to step 448 in FIG. 4.

When a post-pace intrinsic VS event occurs first following the pacing sequence, then the method 746 proceeds to step 750, where the IMD determines whether the post-pace intrinsic VS event occurs more than a certain amount of time (e.g., >50 milliseconds) before a post-pace intrinsic AS event following the pacing sequence.

When the IMD determines that the post-pace intrinsic VS event occurs less than a certain amount of time (e.g., <50 milliseconds) before a post-pace intrinsic AS event following the pacing sequence, the method 746 proceeds from step 750 to step 752 where a AT/SVT type rhythm is detected. In other words, in this implementation, the tachycardia can also be deemed to be an AT/SVT type rhythm type rhythm if a post-pace intrinsic VS event occurs less than a certain amount of time (e.g., <50 milliseconds) before a post-pace intrinsic AS event following the pacing sequence. The method 746 then proceeds to step 448 in FIG. 4. On the other hand, when a post-pace intrinsic VS event occurs more than a certain amount of time (e.g., >50 milliseconds) before a post-pace intrinsic AS event following the pacing sequence, the method 746 proceeds to step 754 where a VT type rhythm or VF type rhythm is detected. The method 746 then proceeds to step 350 in FIG. 3A or step 330 in FIG. 3B. Thus, the diagnostic/therapeutic pacing techniques disclosed herein can enhance a detection algorithm's ability to distinguish between an atrial tachycardia (AT)/supraventricular tachycardia (SVT) type rhythms and ventricular tachycardia (VT)/ventricular fibrillation (VF) type rhythms.

Thus, an episode structure for detection algorithm is provided which incorporates a diagnostic/therapeutic pacing algorithm so that detection and therapy are integrated more closely. Diagnostic/therapeutic pacing is a method for discriminating SVT from VT on the basis of the physiologic response to ATP-like pacing sequences that may be delivered to either the atrium or the ventricle or both simultaneously. The pacing sequence can be both therapeutic and, if unsuccessful, diagnostic. This pacing sequence may terminate the tachyarrhythmia in which case the device episode should be terminated. If the tachyarrhythmia continues, then the response can be used to classify the rhythm as either VT or SVT. When classified as VT, the therapy sequence will continue in the usual manner of ICDs with redetection followed by subsequent therapy. When the therapy is pacing, the physiologic response may once again be used to classify the rhythm as VT or SVT if the tachyarrhythmia does not terminate. If upon initial delivery of pacing, the rhythm is classified as SVT, the device episode will transition to a monitor state and deliver no subsequent therapy until such a time that the episode returns to therapy delivery state. This transition may be the result of changes in the tachyarrhythmia AV pattern, morphology or rate or may be the result of elapsed time since previous pacing exceeding some threshold. Thus, the detection algorithm will continue to monitor for evidence that a sustained tachyarrhythmia once classified as SVT, but subsequently accelerating to VT will receive adequate therapy in sufficient time so as to reduce morbidity associated with the tachyarrhythmia.

While at least one example embodiment has been presented in the foregoing detailed description, it should be appreciated that a vast number of variations exist. It should also be appreciated that the example embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method for operating an implantable medical device (IMD) to treat a tachyarrhythmia in a heart including an atrium and a ventricle, the method comprising:
classifying a tachyarrhythmia of the heart based on one or more supraventricular tachycardia (SVT) rejection rules, wherein at least one of the one or more SVT rejection rules differentiates between a first group of tachyarrhythmias that do not require treatment and a second group of tachyarrhythmias that possibly require treatment; and after classifying the tachyarrhythmia as being within the second group of tachyarrhythmias based on the one or more SVT rejection rules, performing diagnostic/therapeutic pacing to further discriminate the tachyarrhythmia as being within a first sub-group of tachyarrhythmias or a second sub-group of tachyarrhythmias which are to be treated by applying a ventricular tachycardia (VT)/ventricular fibrillation (VF) therapy sequence, wherein performing diagnostic/therapeutic pacing to further discriminate the tachyarrhythmia as being within the first sub-group of tachyarrhythmias or the second sub-group of tachyarrhythmias comprises:
determining a first one of an atria or a ventricle to respond with an electrical event to the diagnostic/therapeutic pacing; and
determining that the tachyarrhythmia is within the first sub-group of tachyarrhythmias or the second sub-group of tachyarrhythmias based on the first one of the atria or the ventricle to respond with the electrical event to the diagnostic/therapeutic pacing.

2. A method according to claim 1, wherein the first group of tachyarrhythmias that do not require treatment comprise: an atrial fibrillation (AF) type heart rhythm, a AV nodal reentrant tachycardia (AVNRT) type heart rhythm, and a Sinus Tachycardia (ST) type heart rhythm, the second group of tachyarrhythmias that possibly require treatment comprise: an atrial tachycardia (AT) type heart rhythm, a supraventricular tachycardia (SVT) type heart rhythm, a ventricular tachycardia (VT) type heart rhythm, and a ventricular fibrillation (VF) type heart rhythm, wherein the first sub-group of tachyarrhythmias comprise: atrial tachycardia (AT) type heart rhythms and supraventricular tachycardia (SVT) type heart rhythms, and wherein the second sub-group of tachyarrhythmias comprise: ventricular tachycardia (VT) type heart rhythms and ventricular fibrillation (VF) type heart rhythms.

3. A method according to claim 1, further comprising:
applying the VT/VF therapy sequence to at least one of the atrium and the ventricle when one of the second sub-group of tachyarrhythmias is detected based on the diagnostic/therapeutic pacing.

4. A method according to claim 1, wherein the VT/VF therapy sequence is applied to at least one of the atrium and the ventricle to terminate a tachycardia when one of the second sub-group of tachyarrhythmias is detected based on the diagnostic/therapeutic pacing.

5. An implantable medical device (IMD) configured to treat a tachyarrhythmia in a heart, the IMD comprising:
a processor configured to:
classify a tachyarrhythmia of the heart based on one or more supraventricular tachycardia (SVT) rejection rules, wherein at least one of the one or more SVT rejection rules differentiates between a first group of tachyarrhythmias that do not require treatment and a second group of tachyarrhythmias that possibly require treatment; and after classification of the tachyarrhythmia as being within the second group of tachyarrhtymias based on the one or more SVT rejection rules, control the performance of diagnostic/therapeutic pacing by a therapy module to further discriminate the tachyarrhythmia as being within a first sub-group of tachyarrhythmias or a second sub-group of tachyarrhythmias which are to be treated by applying a ventricular tachycardia (VT)/ventricular fibrillation (VF) therapy sequence, wherein performing diagnostic/therapeutic pacing to further discriminate the tachyarrhythmia as being within the first sub-group of tachyarrhythmias or the second sub-group of tachyarrhythmias comprises:

determining a first one of an atria or a ventricle to respond with an electrical event to the diagnostic/therapeutic pacing; and determining that the tachyarrhythmia is within the first sub-group of tachyarrhythmias or the second sub-group of tachyarrhythmias based on the first one of the atria or the ventricle to respond with the electrical event to the diagnostic/therapeutic pacing.

6. An implantable medical device according to claim 5, wherein the first group of tachyarrhythmias that do not require treatment comprise: an atrial fibrillation (AF) type heart rhythm, a AV nodal reentrant tachycardia (AVNRT) type heart rhythm, and a Sinus Tachycardia (ST) type heart rhythm, and wherein the second group of tachyarrhythmias that possibly require treatment comprise: an atrial tachycardia (AT) type heart rhythm, a supraventricular tachycardia (SVT) type heart rhythm, a ventricular tachycardia (VT) type heart rhythm, and a ventricular fibrillation (VF) type heart rhythm, wherein the first sub-group of tachyarrhythmias comprise: atrial tachycardia (AT) type heart rhythms and supraventricular tachycardia (SVT) type heart rhythms, and wherein the second sub-group of tachyarrhythmias comprise: ventricular tachycardia (VT) type heart rhythms and ventricular fibrillation (VF) type heart rhythms.

7. An implantable medical device according to claim 5, further comprising:

a first lead configured to be implanted into a ventricle of the heart; and a second lead configured to be implanted into an atrium of the heart, wherein the therapy module is coupled to the processor, the first lead, and the second lead, and wherein the therapy module is configured to deliver a ventricular tachycardia (VT)/ventricular fibrillation (VF) therapy sequence of electrical pulses to at least one of the ventricle via the first lead or the atrium via the second lead, when the processor detects one of the second sub-group of tachyarrhythmias based on the diagnostic/therapeutic pacing.

8. An implantable medical device according to claim 7, wherein the processor, when performing diagnostic/therapeutic pacing, is further configured to determine whether the tachyarrhythmia exhibits a pattern of atrial events and ventricular events that requires a VT/VF therapy sequence based on whether the number of atrial events is:

greater than the number of ventricular events, substantially equal to the number of ventricular events, or less than the number of ventricular events.

9. An implantable medical device according to claim 8, wherein the diagnostic/therapeutic pacing sequence is applied to at least one of the atrium and the ventricle to control the heart rhythm to aid in discriminating between the first sub-group of tachyarrhythmias and the second sub-group of tachyarrhythmias.

10. An implantable medical device according to claim 9, wherein the processor, when performing diagnostic/therapeutic pacing, is further configured to determine the response of the heart to the diagnostic/therapeutic pacing sequence.

11. An implantable medical device according to claim 10, wherein the processor is further configured to perform normal rhythm processing when the heart rhythm following the diagnostic/therapeutic pacing sequence indicates that the diagnostic/therapeutic pacing sequence has terminated the tachyarrhythmia.

12. An implantable medical device (IMD) configured to treat a tachyarrhythmia in a heart, the IMD comprising:

a processor configured to:
classify a tachyarrhythmia of the heart based on one or more supraventricular tachycardia (SVT) rejection rules, wherein at least one of the one or more SVT rejection rules differentiates between a first group of tachyarrhythmias that do not require treatment and a second group of tachyarrhythmias that possibly require treatment; and after classification of the tachyarrhythmia as being within the second group of tachyarrhtymias based on the one or more SVT rejection rules, control the performance of diagnostic/therapeutic pacing by a therapy module to further discriminate the tachyarrhythmia as being within a first sub-group of tachyarrhythmias or a second sub-group of tachyarrhythmias which are to be treated by applying a ventricular tachycardia (VT)/ventricular fibrillation (VF) therapy sequence;

a first lead configured to be implanted into a ventricle of the heart;

a second lead configured to be implanted into an atrium of the heart, wherein the therapy module is coupled to the processor, the first lead, and the second lead, and wherein the therapy module is configured to deliver a ventricular tachycardia (VT)/ventricular fibrillation (VF) therapy sequence of electrical pulses to at least one of the ventricle via the first lead or the atrium via the second lead, when the processor detects one of the second sub-group of tachyarrhythmias based on the diagnostic/therapeutic pacing, wherein the processor, when performing diagnostic/therapeutic pacing, is further configured to determine whether the tachyarrhythmia exhibits a pattern of atrial events and ventricular events that requires a VT/VF therapy sequence based on whether the number of atrial events is:

greater than the number of ventricular events, substantially equal to the number of ventricular events, or less than the number of ventricular events, wherein the diagnostic/therapeutic pacing sequence is applied to at least one of the atrium and the ventricle to control the heart rhythm to aid in discriminating between the first sub-group of tachyarrhythmias and the second sub-group of tachyarrhythmias, wherein the processor, when performing diagnostic/therapeutic pacing, is further configured to determine the response of the heart to the diagnostic/therapeutic pacing sequence, and wherein the processor is further configured to wait for a trigger event when the heart rhythm in response to the diagnostic/therapeutic pacing sequence is indicative of a supraventricular tachycardia (SVT) type rhythm, wherein the trigger event indicates that the heart rhythm as originally diagnosed based on diagnostic/therapeutic pacing has changed and is to be re-evaluated.

13. An implantable medical device according to claim 10, wherein the processor is further configured to instruct the therapy module to apply a VT/VF therapy sequence when the heart rhythm in response to the diagnostic/therapeutic pacing sequence is indicative of a ventricular tachycardia (VT) type rhythm.

14. A method according to claim 1, wherein performing diagnostic/therapeutic pacing to further discriminate the tachyarrhythmia as being within the first sub-group of tachyarrhythmias or the second sub-group of tachyarrhythmias further comprises, in response to the diagnostic/therapeutic pacing, analyzing sensed electrical events of the heart over time to determine whether the tachyarrhythmia is within the first sub-group of tachyarrhythmias or the second sub-group of tachyarrhythmias.

* * * * *